United States Patent [19]

Rhum

[11] Patent Number: 4,649,920

[45] Date of Patent: Mar. 17, 1987

[54] COATED SUTURE

[75] Inventor: Joseph D. Rhum, Old Lyme, Conn.

[73] Assignee: Pfizer Hospital Products Group, Inc., New York, N.Y.

[21] Appl. No.: 824,348

[22] Filed: Jan. 30, 1986

[51] Int. Cl.⁴ .............................................. A61L 17/00
[52] U.S. Cl. .................................................. 128/335.5
[58] Field of Search ................ 128/335.5, 1 R; 427/2; 428/378, 377, 473

[56] References Cited

U.S. PATENT DOCUMENTS 3,665,927 5/1972 Kurtz ................................ 128/335.5
3,896,814 7/1975 Vivien ............................... 128/335.5

Primary Examiner—Gregory E. McNeill
Attorney, Agent, or Firm—Charles J. Knuth; Peter C. Richardson; Robert F. Sheyka

[57] ABSTRACT

There is disclosed an improved absorbable surgical suture. The suture is coated with an absorbable composition consisting essentially of a high molecular weight poly(alkylene oxide).

13 Claims, No Drawings

COATED SUTURE

BACKGROUND OF THE INVENTION

The present invention relates to the field of absorbable sutures. More particularly, the present invention relates to a coated suture having improved tie-down properties.

Suture materials are generally classified as absorbable or non-absorbable, with each type of suture being preferred for different applications. Absorbable suture materials are preferred for applications in which the sewn tissues after healing will hold together without suture reinforcement and in which a non-absorbed suture material may provide the possibility of an adverse body reaction over an extended period of time. Suture materials are considered to be absorbable if they disappear from the sewn tissue within a year after surgery, but most absorbable suture materials disappear within shorter periods of time.

The most commonly employed absorbable suture materials are catgut and extruded collagenous materials. More recently sutures have been developed from synthetic polymers which are absorbable, strong, uniform and dimensionally stable, storable in the dry state and sterilizable.

A significant problem associated with the early synthetic absorbable sutures was difficulty in knot placement. The braid was rough, preventing the surgeon from sliding the knots down the suture and locating those knots accurately for good tissue approximation. To solve this problem, various coating materials have been applied to absorbable sutures. A number of United States patents disclose the use of different coating materials.

U.S. Pat. No. 4,027,676 issued June 7, 1977 discloses an absorbable suture coated with a multicomponent composition comprising (a) an absorbable film-former, (b) an absorbable lubricant, and (c) an absorbable hydrophobic material. This coating has the effect of stiffening the suture so it becomes wire-like rather than soft, smooth and flexible.

U.S. Pat. No. 4,047,533 issued Sept. 13, 1977 discloses an absorbable suture coated with a block copolymer of polyoxyethylene and polyoxypropylene. This coating provides good knot slip-down but knot security is lost and the surgeon must tie four or five knots instead of three to maintain a stitch securely.

U.S. Pat. No. 3,896,814 issued July 29, 1975 discloses the use of a low molecular weight (400) poly(alkylene oxide) as a hygroscopic agent to improve the suppleness of collagen sutures. In the above patent, the low molecular weight poly(alkylene oxide) is used as a humectant for retaining water in the collagen fiber.

Thus, there is a continuing need for a coating for an absorbable suture resulting in a suture having simultaneous improvement in knot security, knot slip-down and hand.

SUMMARY OF THE INVENTION

In accordance with the present invention, there is disclosed a novel bioabsorbable coating for absorbable sutures. The novel coating consists of a high molecular weight poly(alkylene oxide). By the term "high molecular weight poly(alkylene oxide)" is meant a poly(alkylene oxide) of a molecular weight ranging from 100,000 to 5,000,000 with a preferred range from about 250,000 to about 5,000,000. A preferred poly(alkylene oxide) is poly(ethylene oxide). The novel coating can be applied to any suture, including polyglycolide and polylactide sutures. The present invention also comprises a suture attached to a sterile surgical needle and a sterile package containing the suture attached to a sterile surgical needle.

DETAILED DESCRIPTION OF THE INVENTION

The coating composition of the present invention may be applied to any suture where it is desired to improve fiber lubricity, suture tie-down characteristics or the like. Examples of suture compositions include synthetic absorbable sutures including polylactide, polyglycolide, and copolymers of lactide and glycolide with each other and with other reactive monomers such as those described in, for example, U.S. Pat. No. 3,936,952 and U.S. Pat. No. 2,683,136, which patents are incorporated herein by reference. Such preferred suture compositions are referred to herein as simply polymers and copolymers of lactide and glycolide.

The suture onto which the coating composition of the present invention is to be applied can be in the form of a monofilament or a plurality of the component filaments may be combined into a multifilament braid. The monofilament or multifilament suture can be any desired length. Needles may be attached to the sutures. The coated sutures, with or without needles, are generally packaged in sterile enclosures to maintain sterility until time of use.

The coating composition of the present invention comprises a high molecular weight poly(alkylene oxide). Preferred high molecular weight poly(alkylene oxide(s) include poly(ethylene oxide), poly(propylene oxide) and poly(alkylene oxides) of up to 6 carbon atoms in the alkylene group. Preferred high molecular weight poly(alkylene oxides) are those commercially available from Union Carbide under the trade name POLYOX ®. These are water-soluble, non-ionic poly(ethylene oxide) homopolymers ranging in molecular weight from one hundred thousand to five million. Other high molecular weight poly(alkylene oxides) are commercially available from Aldrich Chemical. In the preferred embodiment of the present invention, the poly(alkylene oxide) coating composition has a molecular weight ranging from about 250,000 to about 5,000,000 daltons.

The coating composition of the present invention may be applied to the suture and then the coated suture, with or without an attached needle, can, if desired, be sterile packaged.

Methods of application of the coating composition to the suture include moving the suture through a receptacle containing the coating composition dissolved in an appropriate solvent, moving the suture past a brush or an applicator wetted with the solution or past one or more spray nozzles dispensing the solution as droplets.

If it is desired to apply the poly(alkylene oxide) coating composition of the present invention in a solid form, the coating composition may be applied to the suture by passing the suture over or between solid blocks of the coating composition which is transferred to the suture by a rubbing action.

If a multifilament suture is to be coated with the composition of the present invention, it is not necessary that every filament within the suture be individually or completely coated. In most instances, however, the coating composition will penetrate into the braided suture structure.

Suitable solvents into which the present coating composition may be dissolved include methylene chloride, propylene glycol mono-methyl ether (DOWANOL ® PM), water, acetonitrile, acetone, and ethanol.

The amount of coating composition applied to the suture, or the coating add-on, will vary depending upon the construction of the fiber, e.g., the number of filaments and tightness of braid or twist and the nature of the coating composition, i.e. solution or solid. In general, a coating composition applied to the suture will constitute from about 0.1 to about 20 percent by weight of the coated fiber with a preferred range of from about 3 to about 15 percent by weight. The level of coating add-on imparting maximum desired characteristics, such as tie down performance, is readily determined experimentally for any particular fiber-coating system.

The coating composition may, if desired, also contain components other than those discussed above for other useful purposes including dyes, antibiotics, antiseptics, anesthetics and anti-inflammatory agents.

Having described the invention in general terms, reference is now made to specific examples thereof.

EXAMPLE 1

Eighteen inch lengths of Dexon "S" polyglycolic acid braided suture from American Cyanamid Corporation and Pfizer Inc. Hospital Product Group dyed, braided and heat-stretched PGA (Polyglycolic acid) size 4-0 were immersed in 100 cc of solution of various coating agents in methylene chloride. The concentrations of the coating agents are given in grams per 100 cc of solution (% w/v). The sutures were immersed for at least 2 minutes, then hung to air dry in a vertical position. The coating add-on was determined by weighing a length of suture before and after coating on an analytical balance and averaging the results of three separate threads. Ten to twenty 18 inch coatings on Pfizer's 4-0 PGA were prepared; two 18 inch specimens of each coating on 4-0 Dexon were prepared.

The coated sutures were tested by the following techniques:

(a) Slip-Down

A two throw square knot is tied to a firm closed knot but not extremely tightly, the long ears grasped, and pulled apart. If the thread is drawn through the knot, giving the appearance of the knot slipping down the braid, that is denoted good slip-down. If the knot binds and will not slide when the ears are pulled apart, then there is no slip-down.

(b) Knot-Security

A triple throw square knot is firmly tied creating a loop in the length of the suture that is large enough so that when the loop is cut opposite to the knot, the two equal arms of the cut loop can be held in a tensile testing machine. The cut lengths of the loop are on the patient's side of the knot. The lengths of suture (the free ends) on the other side of the knot (the surgeon's side) are carefully trimmed before cutting the loop to a specified length, such as 0.1 inch or 0.2 inch, etc. called ears. The loop is then cut to create the patient's side ends. These are then clamped in a tensile testing machine and the suture is pulled until the knot slips out or the suture breaks. If the knot slips out, for the next trial an additional square knot throw is added to the knot. The knot security is the number of square knot throws required to cause the suture to break reliably at the knot instead of slipping out. The tensile testing machine used was a Scott Tensilometer or an I-Mass Model SP-101 slip/peel tester modified to permit the attachment of fibers. Coated sutures were evaluated for texture, the results of which are summarized in Table 1. The coated sutures were also evaluated for knot security and snug-down rating, the results of which are summarized in Table 2.

TABLE 1

| COATED SUTURE - TEXTURE EVALUATIONS | | | | |
|---|---|---|---|---|
| Suture | Coating Material | $CH_2Cl_2$ Solution Conc % (w/v) | Add-On Dry Wt % | Texture After Coating |
| Dexon "S" | Poly(ethylene glycol) M.W. 400 | 10% | 4.44 | Slightly stiff and Smooth |
| " | Poly(ethylene glycol M.W. 14,000 | 10% | 16.36 | Slightly Stiff & Smooth |
| " | Poly(ethylene oxide) M.W. 100,000 | 1.0% | 2.90 | Soft & Silky |
| " | Poly(ethylene oxide) M.W. 900,000 | 1.0% | 3.09 | Soft & Smooth |
| Pfizer | Poly(ethylene oxide) M.W. 100,000 | 7.5% | 15.43 | Stiff & Slightly Rough |
| " | Poly(ethylene oxide) M.W. 100,000 | 5.0% | 7.01 | Stiff & Slightly Rough |
| " | Poly(ethylene oxide) M.W. 100,000 | 2.5% | 3.33 | Stiff & Slightly Rough |
| " | Poly(ethylene oxide) M.W. 900,000 | 0.5% | 2.26 | Soft & Silky |
| " | Poly(ethylene oxide) M.W. 900,000 | 1.0% | 3.33 | Soft & Silky |
| " | Poly(ethylene glycol) M.W. 14,000 | 2.5% | 8.16 | Slightly Stiff & Smooth |
| " | Poly(ethylene glycol) M.W. 14,000 | 7.5% | 11.51 | Slightly Stiff & Smooth |
| " | Poly(ethylene glycol) M.W. 14,000 | 5.0% | 11.20 | Slightly Stiff & Smooth |

TABLE 2
COATED SUTURE - KNOT SECURITY AND SNUG DOWN RATING

| Suture | Coating Material | Solids Add-On Wt % | Snug Down Rating | Knot Security* 3 Throws - 2/10" Ears |
|---|---|---|---|---|
| Pfizer | Poly(ethylene oxide) M.W. 100,000 | 15.43 | Excellent | 2 knots broke - 1 slipped |
| " | Poly(ethylene oxide) M.W. 100,000 | 7.01 | Excellent | Broke at knot |
| " | Poly(ethylene oxide) M.W. 100,000 | 3.33 | Excellent | 1 broke - 1 slipped |
| " | Poly(ethylene oxide) M.W. 900,000 | 2.26 | Excellent | Broke at knot |
| " | Poly(ethylene oxide) M.W. 900,000 | 3.33 | Excellent | Broke at knot |
| " | Poly(ethylene glycol) M.W. 14,000 | 11.51 | Excellent | Slipped - 1 broke |
| " | Poly(ethylene glycol) M.W. 14,000 | 11.20 | Excellent | Slipped |
| " | Poly(ethylene glycol) M.W. 14,000 | 8.16 | Excellent | 1 broke - 2 slipped |

*3 trials per condition

I claim:

1. An absorbable surgical suture having improved tie down properties characterized in that the surface of the suture is coated with a composition consisting essentially of at least one high molecular weight poly(alkylene oxide).

2. The suture of claim 1 wherein said high molecular weight poly(alkylene oxide) has a molecular weight ranging from about 100,000 to about 5,000,000.

3. The suture of claim 2 wherein said high molecular weight poly(alkylene oxide) has a molecular weight ranging from about 250,000 to about 5,000,000.

4. The suture of claim 1 wherein said suture is a poly(glycolic acid) suture.

5. The suture of claim 1 wherein said suture is a multifilament suture.

6. The suture of claim 5 wherein the multifilament suture is a braided suture.

7. The suture of claim 1 wherein the suture is a monofilament suture.

8. The suture of claim 1 wherein the high molecular weight poly(alkylene oxide) is poly(ethylene oxide).

9. A needled surgical suture comprising at least one surgical suture and one needle characterized in that the surface of the suture is coated with a composition consisting essentially of at least one high molecular weight poly(alkylene oxide).

10. A surgical suture package comprising a sterile enclosure containing a sterile needled surgical suture, the suture characterized in that the surface of the suture is coated with a composition consisting essentially of at least one high molecular weight poly(alkylene oxide).

11. A surgical suture package as in claim 10 wherein the high molecular weight poly(alkylene oxide) is poly(ethylene oxide).

12. A method of suturing by stitching with at least one surgical suture coated with a composition consisting essentially of at least one high molecular weight poly(alkylene oxide).

13. A method as in claim 12 wherein said high molecular weight poly(alkylene oxide) is poly(ethylene oxide).

* * * * *